US00PP15406P2

(12) United States Plant Patent
Olesen et al.

(10) Patent No.: US PP15,406 P2
(45) Date of Patent: Dec. 7, 2004

(54) ROSE PLANT NAMED 'POULPM004'

(50) Latin Name: *Rosa hybrida*
Varietal Denomination: POULpm004

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,757

(22) Filed: Mar. 29, 2004

(51) Int. Cl.[7] ..... A01H 5/00
(52) U.S. Cl. ..... Plt./137
(58) Field of Search ..... Plt./137

*Primary Examiner*—Anne Marie Grunberg
*Assistant Examiner*—Annette H Para

(57) ABSTRACT

A new garden rose plant of the hybrid tea class which has abundant, mauve flowers and attractive foliage. This new and distinct variety has shown to be uniform and stable in the resulting generations from asexual propagation.

2 Drawing Sheets

Botanical classification: *Rosa hybrida.*
Variety denomination: 'POULpm004'.

The present invention constitutes a new and distinct variety of garden rose plant which originated from a controlled crossing between the female seed parent, an unnamed seedling, and the male pollen parent, an unnamed seedling. Both parent plants are non-patented. The two parents were crossed during the summer of 1997 and the resulting seeds were planted in a controlled environment in Fredensborg, Denmark. The new variety is named 'POULpm004'.

The new variety may be distinguished from its unnamed female seed parent by the following combination of characteristics:

1. While the unnamed seed parent has an open flower diameter of 120–140 mm; the same of 'POULpm004' is 80–100 mm.
2. While the petal count of the female parent is very double, the same of 'POULpm004' is double.

The new variety may be distinguished from its unnamed male pollen parent, by the following combination of characteristics:

1. While the unnamed pollen parent has a flower diameter of approximately 60 mm; the same of 'POULpm004' is 80–100 mm.
2. While the unnamed pollen parent has a flower bud length of 45 mm; the same of 'POULpm004' is 30 mm.
3. While the unnamed pollen parent has a pointed ovoid bud form; the same of 'POULpm004' is a globular bud form.

The objective of the hybridization of this rose variety was to create a new and distinct variety for garden use with unique qualities, such as:

1. Uniform and abundant mauve flowers;
2. Vigorous, but compact growth when propagated both as a budded rose and on its own roots;
3. Exceptional rose scent;
4. Disease resistance.

This combination of qualities is not present in previously available commercial cultivars of this type, known to the inventors, and distinguish 'POULpm004' from all other varieties of which we are aware.

As part of their rose development program, L. Pernille Olesen and Mogens N. Olesen germinated the seeds from the aforementioned hybridization in January of 1998 and conducted evaluations on the resulting seedlings in a controlled environment in Fredensborg, Denmark.

'POULpm004' was selected in the spring of 1998 by the inventors as a single plant from the progeny of the aforementioned hybridization.

Asexual reproduction of 'POULpm004' by traditional budding and rooted cuttings was first done by L. Pernille and Mogens N. Olesen in their nursery in Fredensborg, Denmark in July, 1998. This initial and other subsequent asexual propagations conducted in controlled environments have demonstrated that the phenotypical characteristics of 'POULpm004' are true to type and are transmitted from one generation to the next.

BRIEF DESCRIPTION OF THE DRAWING

The accompanying color illustration shows as true as is reasonably possible to obtain in color photographs of this type, characteristics of the flower buds, open flowers, leaves, and stems, of 'POULpm004'. Specifically illustrated in SHEET 1:

FIG. 1.1; Stem showing branching, the attachment of leaves, buds, and peduncles, as well as open flowers at various stages of development;

FIG. 1.2; Sepals, receptacle, and peduncle.

Specifically illustrated in SHEET 2:

FIG. 2.1; Flower petals and petaloids, detached;

FIG. 2.2; Mature leaf, upper surface, as well as juvenile leaf;

FIG. 2.3; Bare stems exhibiting thorns.

DETAILED DESCRIPTION OF THE VARIETY

The following is a description of 'POULpm004', as observed in its growth in in a field nursery in Jackson County, Oreg. Observed plants are 3 years of age, and were grown on *Rosa multiflora* understock. Color references are made using The Royal Horticultural Society (London, England) Colour Chart, 1995, except where common terms of color are used.

For a comparison, several physical characteristics of the rose variety 'POULen005', a rose variety from the same inventors described and illustrated in U.S. Plant patent application Ser. No. 10/738,156 and dated Dec. 16, 2003, are compared to 'POULpm004' in Chart 1.

CHART 1

| | 'POULpm004' | 'POULen005' |
|---|---|---|
| General tonality. | White Group 155C with intonations of Purple Group 75C–75D. | Violet Group 84C. |
| Diameter of open flower. | 75 mm. | 80 to 100 mm |
| Petal size. | 62 mm (l) × 50 mm (w). | 60 to 65 mm (l) × 36 mm (w). |

FLOWER AND FLOWER BUD

Blooming habit: Recurrent.

Flower bud:

*Size.*—Upon opening, 30 mm in length from base of receptacle to end of bud. Bud diameter is 23 mm.

*Bud form.*—Globular.

*Bud color.*—As sepals unfold, petals are Red Group 39A with intonations of Purple Group Purple Group 79C and Purple Group 76A. At ¼ opening petals are Violet Group 84C with intonations of White Group 155B.

*Sepals.*—Upper Surface: Upper Surface is Yellow-Green Group 145C in color. Moderately pubescent. Lower Surface: Lower Surface is Yellow-Green Group 144A. Light anthocyanic pigments the color of Greyed-Orange Group 169A–171A observed. Texture is smooth with scant stipitate glands. Shape: Sepal apex is cirrhose. Base is flat at union with receptacle. Sepal Margin: Margins have medium foliaceous appendages on three of the five sepals. Size: 26 mm long by 11 mm wide.

*Receptacle.*—Surface Texture: Smooth. Shape: Funnel shaped. Size: 6 mm in length by 5 mm in width. Color: Yellow-Green Group 144B.

*Peduncle.*—Surface: Smooth and glabrous. Length: 53 to 60 mm average length. Color: Yellow-Green Group 144B. Strength: Strong.

*Borne.*—Multiples of 7 buds per flowering stem.

Flower bloom:

*Fragrance.*—Strong perfume scent.

*Duration.*—The blooms have a duration on the plant of approximately 10 to 14 days. Petals fall cleanly away from plant.

*Size.*—Flower diameter is 75 mm when open. Flower depth is 45 to 50 mm.

*Form.*—Globular.

*Side view flower form.*—Upon opening; The upper portion is flat. The lower portion is concave. Open flowers; The upper portion is flat. The lower portion is concave.

*Petalage.*—97 petals on average under normal conditions with 23 petaloids.

Color:

*Upon opening, petals.*—Outermost petals: Outer side: White Group 155B, with intonations of Purple Group 75C–75D at marginal zone. Inner side: White Group 155C. Innermost petals: Outer Side: White Group 155B with light intonations of Purple Group 75C–75D at marginal zone. Inner Side: White Group 155C.

*Upon opening, basal petal spots.*—No distinctive coloration at the petal base observed.

*After opening, petals.*—Outermost petals: Outer side: White Group 155B with intonations of Purple Group 75C–75D at marginal zone. Inner side: White Group 155C. Innermost petals: Outer side: White Group 155B with intonations of Purple Group 75C–75D at marginal zone. Inner Side: White Group 155C.

*After opening, basal petal spots.*—No distinctive coloration at the petal base observed.

General tonality: On open flower White Group 155C with intonations of Purple Group 75C–75D. No change in the general tonality at the end of the $10^{th}$ day.

Petals:

*Petal reflex.*—Strongly reflexed.

*Margin.*—Entire and uniform.

*Shape.*—Apex is round. Base shape varying from acute to round.

*Size.*—62 mm (l) 50 mm (w).

*Texture.*—Smooth.

*Thickness.*—Thick.

*Arrangement.*—Not formal.

Petaloids:

*Quantity.*—20 to 30.

*Color.*—Upper surface: White Group 155C. Lower surface: White Group 155B with intonations of Purple Group 75C–75D.

*Size.*—40 mm (l)×18 mm (w).

Reproductive organs:

*Pollen.*—None observed.

*Anthers.*—Size: 3 mm in length. Color: Yellow-Orange Group 21B. Quantity: 182 (actual count).

*Filaments.*—Color: Yellow Group 4C. Length: 10 mm.

*Pistils.*—Length: 10 mm. Quantity: 132 (actual count).

*Stigmas.*—Level relative to the length of the filaments and the height of the anthers. Color: Yellow-White Group 158A.

*Styles.*—Color: Yellow-Green Group 150D. Other observed intonations are Red Group 46C.

*Hips.*—Non Observed in the field nursery in Jackson County, Oreg.

PLANT

Plant growth: Narrow and bushy. When grown as a budded field grown plant on *Rosa multiflora* understock, the average height of the plant is 60 to 100 cm.

Stems:

*Color.*—Young wood: Yellow-Green Group 144A. Older wood: Yellow-Green Group 146A.

*Surface texture.*—Young wood: Smooth. Older wood: Smooth.

Thorns:

*Incidence.*—8 thorns per 10 cm of stem.

*Size.*—Average length: 7 mm.

*Color.*—Greyed-Orange Group 165B.

*Shape.*—Deeply concave.

Plant foliage: Normal number of leaflets on normal leaves in middle of the stem: 5 leaflets.

*Compound leaf.*—150 mm (l)×120 mm (w).

*Color.*—Mature Foliage: Upper surface is: Yellow-Green Group 147A. Lower surface is: Yellow-Green Group 147B. Juvenile foliage: Upper surface is: Yellow-Green Group 147A to 146A. Lower surface is: Yellow-Green Group 147B.

Plant leaves and leaflets:

*Stipules.*—Size: 20 mm in length. Shape: Linear, slightly broad based with outward extending apecies.

Margins: Finely serrated with few stipitate glands. Color: Yellow-Green Group 144A.

*Petiole*.—Length: 43 mm. Above: Color: Yellow-Green Group 144B. Anthocyanin: None. Underneath: Thorns.

*Rachis*.—Length: 73 mm. Above: Color: Yellow-Green Group 144B. Underneath: Thorns.

*Leaflet*.—Edge: Finely serrated. Leaflet size: 72 mm (l)×55 mm (w). Shape: Ovate to round. Base is rounded. Apex is somewhat round to cuspidate. Texture: Smooth. Thickness: Thick. Arrangement: Odd pinnate. Venation: Reticulate. Glossiness: Very glossy.

Disease resistance: Above average resistance to mildew, rust, black spot, and Botrytis under normal growing conditions in Jackson County, Oreg.

Cold hardiness: The variety 'POULpm004' has been found to be cold tolerant to USDA Cold Hardiness Zone 6.

We claim:

1. A new and distinct variety of rose plant of the hybrid tea rose class, substantially as herein illustrated and described as a distinct and novel rose variety due to its abundant mauve flowers, disease resistance, and extended period of bloom.

* * * * *

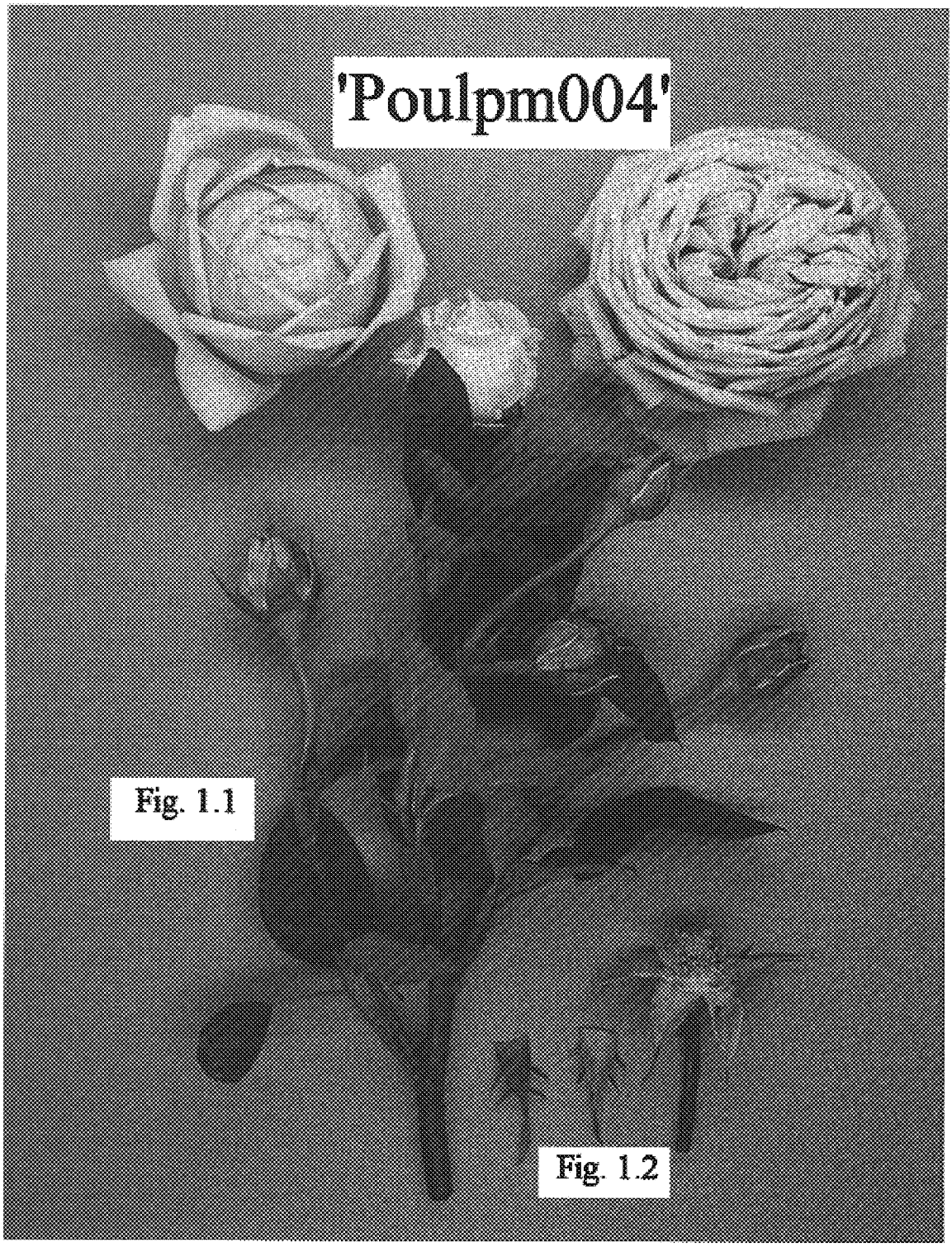
'Poulpm004'
Fig. 1.1
Fig. 1.2

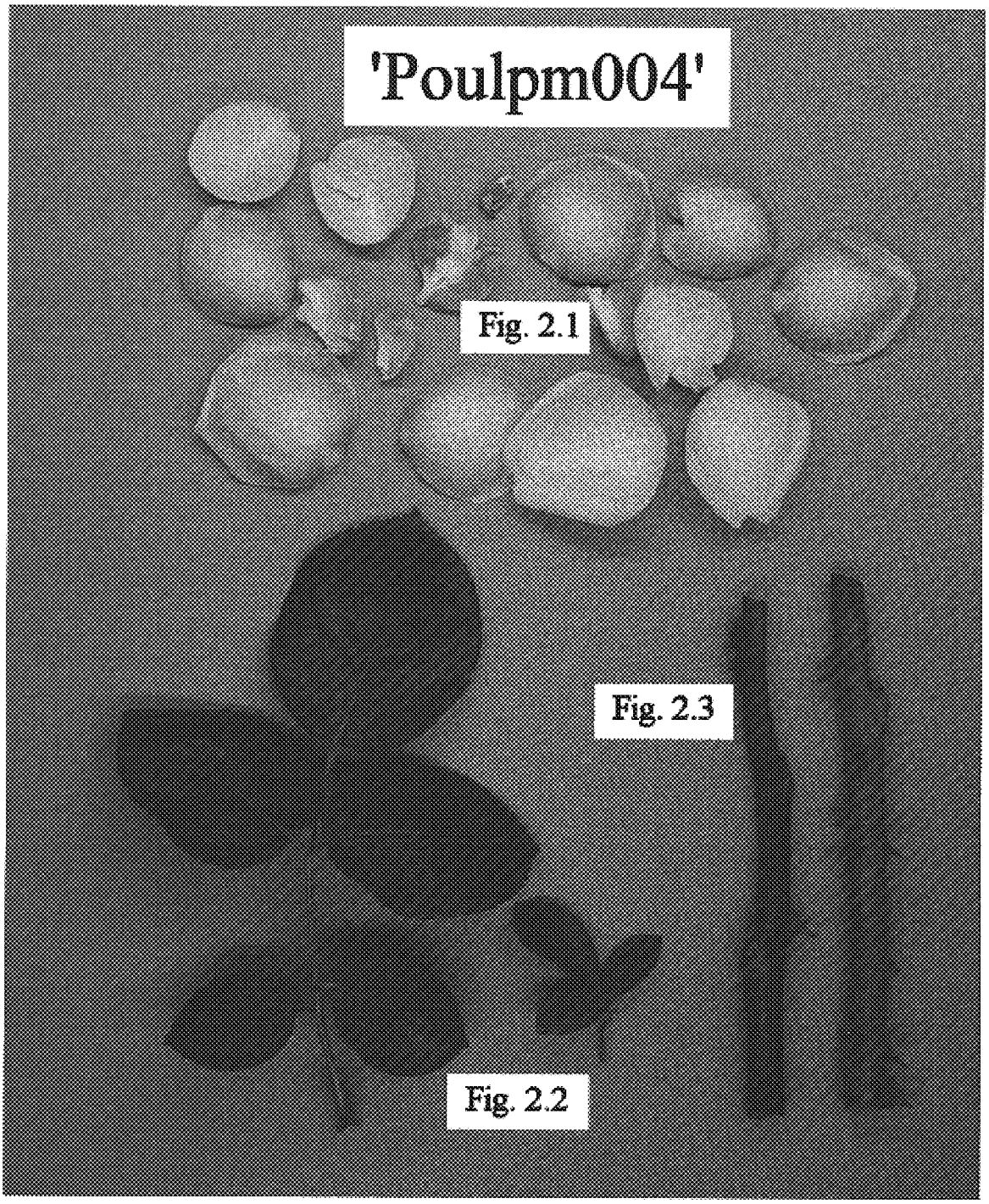
'Poulpm004'
Fig. 2.1
Fig. 2.3
Fig. 2.2